United States Patent [19]
Gomez

[11] Patent Number: 6,053,166
[45] Date of Patent: Apr. 25, 2000

[54] INTUBATING ASSEMBLY

[76] Inventor: Richard J. Gomez, 17830 SW. 152nd Ave., Miami, Fla. 33196

[21] Appl. No.: 09/032,017

[22] Filed: Feb. 9, 1998

[51] Int. Cl.[7] .................................................. A61M 16/00
[52] U.S. Cl. .............................. 128/200.26; 128/207.14
[58] Field of Search ........................ 128/200.26, 217.14, 128/912, DIG. 26

[56] References Cited

U.S. PATENT DOCUMENTS

| | | | |
|---|---|---|---|
| 2,498,692 | 2/1950 | Mains | 604/96 |
| 3,044,461 | 7/1962 | Murdock | 128/207.14 |
| 3,060,972 | 10/1962 | Sheldon | 138/120 |
| 3,968,800 | 7/1976 | Vilasi | 128/207.14 |
| 4,067,331 | 1/1978 | Berman | 128/200.26 |
| 4,211,234 | 7/1980 | Fisher | 128/200.26 |
| 4,529,400 | 7/1985 | Scholten | 128/207.14 |
| 5,323,771 | 6/1994 | Fisher et al. | 128/207.14 |
| 5,403,297 | 4/1995 | Imran | 604/281 |
| 5,498,231 | 3/1996 | Franicevic | 128/207.14 |
| 5,623,924 | 4/1997 | Lindenman et al. | 128/207.17 |
| 5,791,338 | 8/1998 | Merchant et al. | 128/207.14 |

*Primary Examiner*—John G. Weiss
*Assistant Examiner*—Todd M. Martin
*Attorney, Agent, or Firm*—Quarles & Brady

[57] ABSTRACT

An intubating assembly used to position an intubation tube having a distal end, a proximal end and a generally resilient tubular configuration, into a trachea of a patient, the intubating assembly having a guide assembly that receives the intubation tube therein and conforms the intubation tube to its configuration. The guide assembly includes first and second introduction segments hingedly coupled to one another and positionable between a closed orientation, which defines a generally curved configuration of the guide assembly, and an open orientation, which defines a generally straight configuration of the guide assembly. The intubating assembly further includes a positioning assembly structured to selectively position the first and second introduction segments between the open orientation, wherein the intubation tube is generally straightened to facilitate direct introduction thereof into an airway of the patient to a point posterior of a tip of an epiglottis of the patient, and the closed orientation, wherein the intubation tube is generally curved in order to angle the distal end thereof towards the trachea of the patient and thereby introduce the intubation tube directly into the trachea of the patient.

20 Claims, 6 Drawing Sheets

INTUBATING ASSEMBLY

BACKGROUND OF THE INVENTION

1. Field of the Invention

The present invention relates to an intubating assembly structured to facilitate the safe, rapid and aligned positioning and introduction of an intubation tube into a trachea of a patient in a manner which minimizes the risk of accidental introduction of the intubation tube into the esophagus, pyriform sinus or vallecula of the patient by guiding the intubation tube through the airway of the patient until it may be directed specifically into the trachea.

2. Description of the Related Art

Frequently, patients undergoing medical treatment and patients in emergency situations experience some form of trauma and/or medical problem that tends to require that they have some breathing assistance or control. As a result, it is frequently necessary to intubate a patient immediately at an emergency site in order to resume breathing, or in a surgical setting when respiratory muscles must be paralyzed.

Specifically, endotracheal intubation of a patient involves the introduction of an elongate, tubular intubation tube through the mouth of a patient and into the trachea of the patient for communication with the lungs of the patient. Once effectively positioned, the intubation tube is connected with a conventional ventilator assembly and is utilized for continuous, direct ventilation of the patient. Unfortunately, however, proper introduction of the intubation tube into the patient's airway can be quite difficult, and often involves extensive training in specialized techniques in order to accomplish it rapidly and effectively.

The most common techniques taught to hospital workers, and especially to emergency medical technicians (EMTs) who must introduce intubation tubes in a rapid, emergency situation, usually require a patient's head be tilted, in order to generally align the patient's mouth with their trachea, followed by a direct introduction of the intubation tube into the patient's airway. While these techniques are theoretically quite effective, normal anatomical limitations in the positioning of the patient's head make it such that direct alignment can generally not be achieved, especially if limitations on the movement of the patient's head are present, and some further manipulation of the intubation tube within the airway of the patient is required. As a result, the most commonly employed technique further involves the grasping of the intubation tube between the technician's fingers and manually introducing the fingers and the intubation tube into the patient's airway as far as possible in order to generally guide the tip of the intubation tube towards the trachea. Still, however, such manual introduction techniques can be quite difficult. For example, unless a technician has generally long fingers, optimal access into the patient's mouth cannot be achieved, and the added width of the technician's fingers may tend to create a tight fit through the patient's mouth, thereby limiting manipulability and further limiting introduction depth. Further, if the patient is conscious, manual introduction can be hazardous to the technician as they are susceptible to being bitten during intubation. Moreover, even with manual introduction, a certain degree of "feeling around" within the patient's airway is still required. Furthermore, because of the degree of head extension necessary for effective intubation, either manually or using some known device, the patient's teeth are often broken because of the force required to manipulate the lower jaw, especially when performed by less experienced clinicians.

As such, a primary reason for the difficulty associated with the accurate introduction of an intubation tube relates to the unavoidable limitations of the human anatomy. Specifically, in addition to limitations associated with opening the mouth to a sufficient access orientation, continuous with a roof of a patient's mouth is the esophagus. As such, if the intubation tube is merely driven along a roof of the mouth, improper intubation into the esophagus will almost certainly be achieved. Conversely, if the intubation tube is driven over the tongue and down a bottom of a throat, a patient's vallecula, a short passage bordered by the epiglottis, is positioned such that intubation into the vallecula will generally result. Indeed, the epiglottis is seen to extend out into the airway so as to effectively guide the intubation tube into the vallecula if the tip of the intubation tube is not generally spaced from the bottom of the patient's mouth and throat. Accordingly, due to the various passages and contours associates with the human anatomy, an effective device which can provide for consistent and rapid introduction of the intubation tube into the appropriate passage, namely the trachea, will be highly beneficial.

Others in the art have sought to provide devices which can more effectively provide for the introduction of an intubation tube. Typically, however, these devices involve some manipulation of the epiglottis and/or vallecula and can independently cause trauma to the patient. More importantly, however, such known devices are often quite large and bulky, and are therefore very difficult to effectively introduce into the patient's airway through the patient's mouth, while still permitting room for manipulation of the intubation tube. For example, one conventionally implemented device includes an elongate, straight "blade" type element which pins the epiglottis down into the vallecula, thereby sealing off the vallecula and providing for straight introduction of the intubation tube along a base of the throat. Unfortunately, however, such a device still requires safe extension thereof beyond the epiglottis, in the same manner as would be required with the intubation tube itself, in order to effectively pull back on the epiglottis and pin it down within the vallecula. Therefore, while facilitating the introduction of the intubation tube, the device itself includes the same problems with proper positioning which are associated with introduction of the intubation tube, namely extending beyond the epiglottis and vallecula, towards the trachea in order to pull down the epiglottis. Conversely, another device which has been developed in an attempt to facilitate introduction of an intubation tube includes a tab-type element which is to be introduced into the vallecula, and thereby abuts the epiglottis. This device includes an internal guideway through which the intubation tube extends, with the tab element extending separately therefrom. Due to the required configurations so as to mate with the vallecula, while sufficiently protruding therefrom in order to provide for effective spaced positioning of the guideway in order to achieve guidance of the intubation tube over the epiglottis, such devices are quite large and bulky, and are very difficult to fit into the patient's mouth, especially if the patient is conscious and traumatized. Moreover, once the intubation tube is positioned, such devices can prove very difficult to remove without pulling on the intubation tube, as they are often very close to a size of a patient's mouth and can pin the intubation tube when being manipulated during withdrawal.

Accordingly, there is still substantial need in the art for an effective device which can substantially assist the introduction of an intubation tube into a patient and does not require over extension of the patient's head, or cause trauma to the patient during use. Such a device should be substantially compact, easy to manipulate, and substantially precise, thereby providing for rapid, safe and effective introduction of an intubation tube, even in emergency situations wherein immediate intubating in order to provide for ventilation of a patient is required, while maintaining the head in a more neutral position. Furthermore, use of such a device should be easily trained, with consistent, accurate results occurring during each use.

SUMMARY OF THE INVENTION

The present invention relates to an intubating assembly. The intubating assembly is structured to position an intubation tube, of the type which typically includes a distal end, a proximal end, and a generally resilient tubular configuration, into a trachea of a patient, thereby providing a means for effectively ventilating the patient.

The intubating assembly of the present invention includes a guide assembly. The guide assembly is structured to extend into the patient's airway and to at least partially receive the intubation tube to be introduced into the patient's trachea therein. Moreover, the guide assembly is structured to at least partially and selectively conform the intubation tube to its configuration. Specifically, the guide assembly includes at least a first introduction segment and a second introduction segment. The first and second introduction segments are hingedly coupled to one another and are positionable between a closed orientation and an opened orientation. The closed orientation is such that it defines a generally curved configuration of the guide assembly, while the open orientation is such that it defines a generally straight or less curved configuration of the guide assembly.

The intubating assembly further includes a positioning assembly. The positioning assembly is structured to selectively position at least the first and second introduction segments between their open orientation and their closed orientation. In particular, when the first and second introduction segments are positioned in the open orientation, the generally straight or less curved configuration of the guide assembly is achieved and as such, the intubation tube disposed in the guide assembly achieves a generally straightened or less curved configuration. Accordingly, direct introduction of the intubation tube into an airway of a patient to a point posterior of a tip of the epiglottis of the patient is effectively and easily achieved. Conversely, when the positioning assembly positions the first and second introduction segments into the closed orientation, the generally curved configuration of the guide assembly is achieved. In this closed orientation, the intubation tube disposed in the guide assembly is generally curved and a distal end thereof is angled towards the trachea of the patient. Accordingly, it is seen that the positioning assembly will preferably be utilized to position the first and second introduction segments in the closed orientation after the intubation tube has been extended to the point posterior of the tip of the epiglottis of the patient. As such, upon angling the distal end up towards the trachea of the patient, subsequent introduction of the introduction tube or the intubation tube further into the airway of the patient directs the introduction tube and/or the intubation tube into the trachea and not into the esophagus of the patient.

It is an object of the present invention to provide an intubating assembly which provides for consistent, accurate and aligned introduction of an intubation tube into the trachea of the patient.

A further object of the present invention is to provide an intubating assembly which is substantially compact and easy to manipulate by a technician in order to provide for accurate introduction of an intubation tube.

A further object of the present invention is to provide an intubating assembly which is substantially easy to use.

Another object of the present invention is to provide an intubating assembly which safely, gently, accurately and effectively guides introduction of an intubation tube posterior of a vallecula and epiglottis of the patient and anterior of an esophagus of a patient in order to effectuate proper positioning in the trachea of the patient.

Also an object of the present invention is to provide an intubating assembly which does not require a technician to introduce their fingers into the patient in order to provide for effective and accurate guiding of the intubation tube.

Yet another object of the present invention is to provide an intubating assembly which can rapidly and accurately introduce an intubating tube in an emergency situation, particularly when extension or manipulation of the head and neck are not possible because of trauma precautions or stiffness of the neck due to contractures.

These and other objects, features and advantageous of the present invention will become more readily apparent from the attached drawings and the detailed description of the preferred embodiment, which follows.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
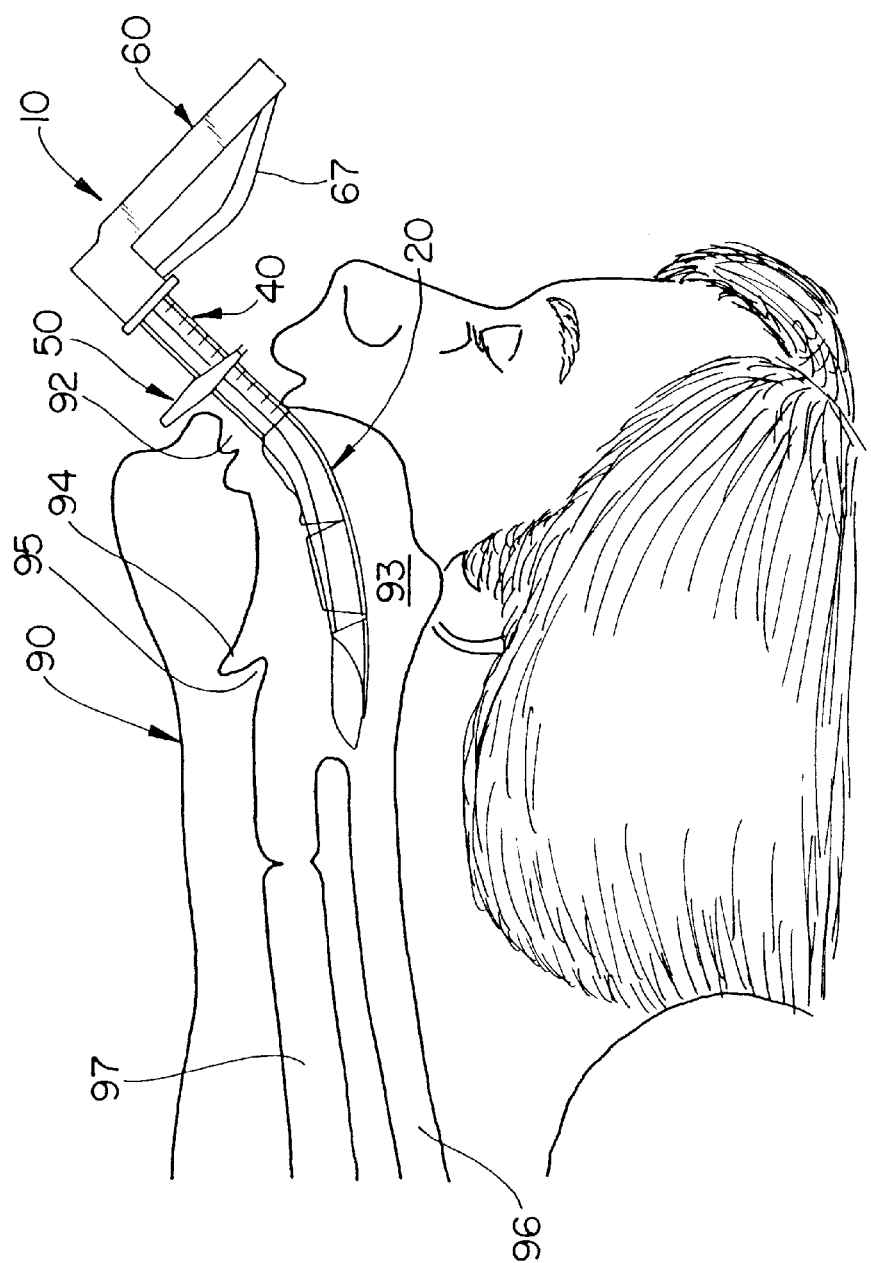
FIG. 1 is a side perspective view illustrating use of the intubating assembly of the present invention with the guide assembly in its open orientation.

Shown throughout the Figures, the present invention is directed towards an intubating assembly, generally indicated as 10. Specifically, the intubating assembly 10 is structured to facilitate the rapid, safe and accurate positioning of an intubation tube 80 into a trachea 97 of a patient 90, preferably through a mouth 92 of the patient 90. The intubation tube 80 is preferably of the type which includes a generally resilient tubular configuration that is open at a distal end 82 and a proximal end 84 thereof. Moreover, the intubation tube 80 is preferably substantially elongate so as to extend well into the trachea 97 of the patient 90, while still protruding from the mouth 92 for normal connection to a ventilation assembly.

Figure 2:
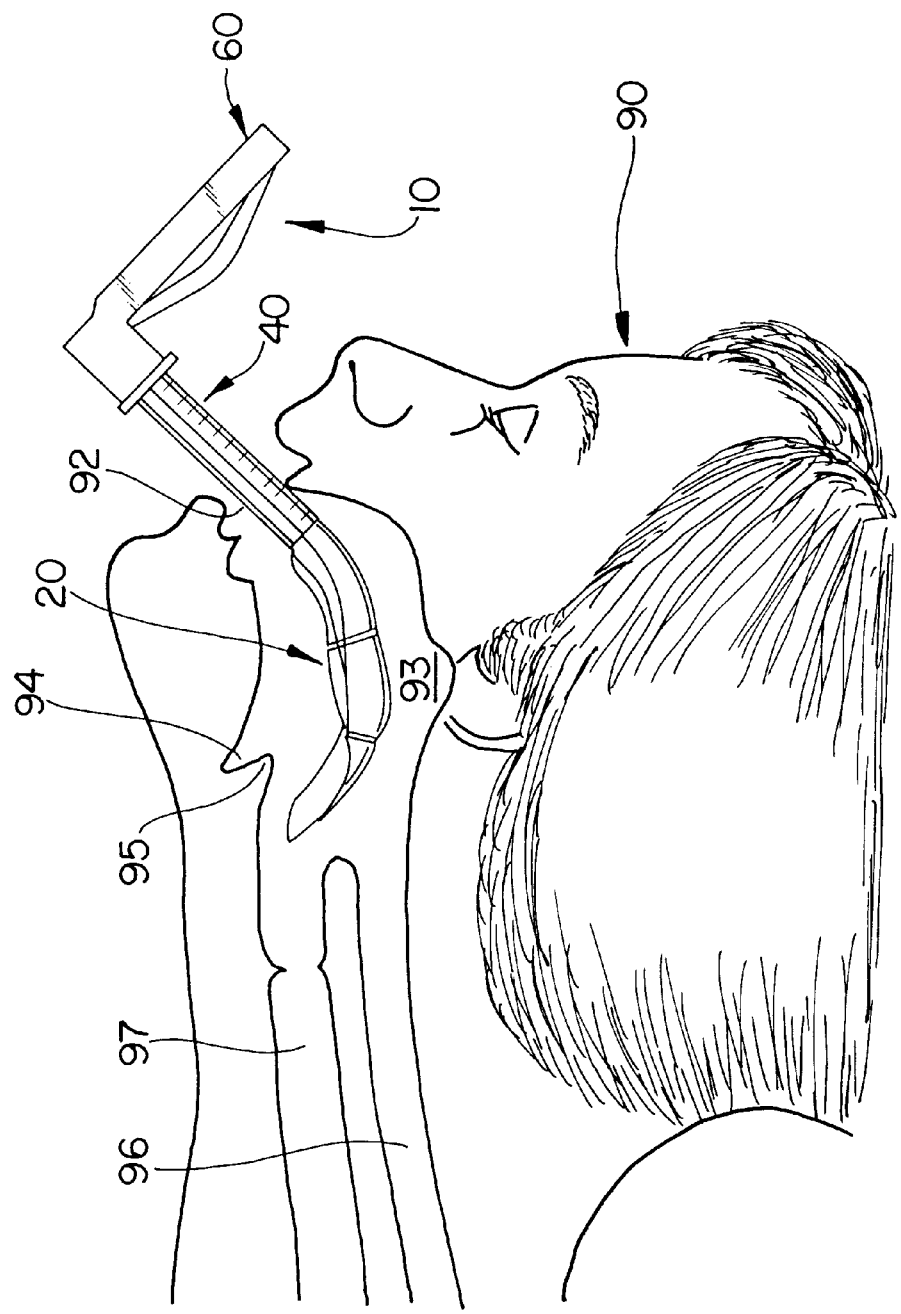
FIG. 2 is a side perspective view illustrating use of the intubating assembly of the present invention with the guide assembly in its closed orientation.
Figure 4:
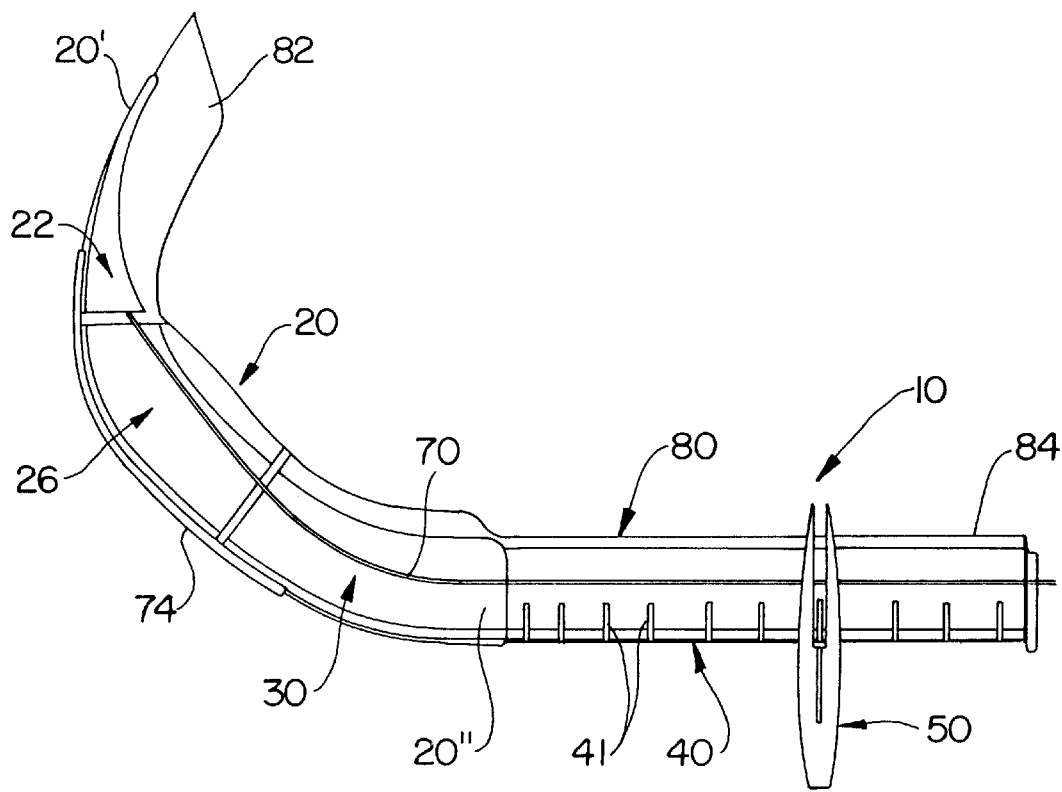
FIG. 4 is an isolated side view of the intubating assembly of the present invention with the guide assembly in its closed orientation.
Figure 5:
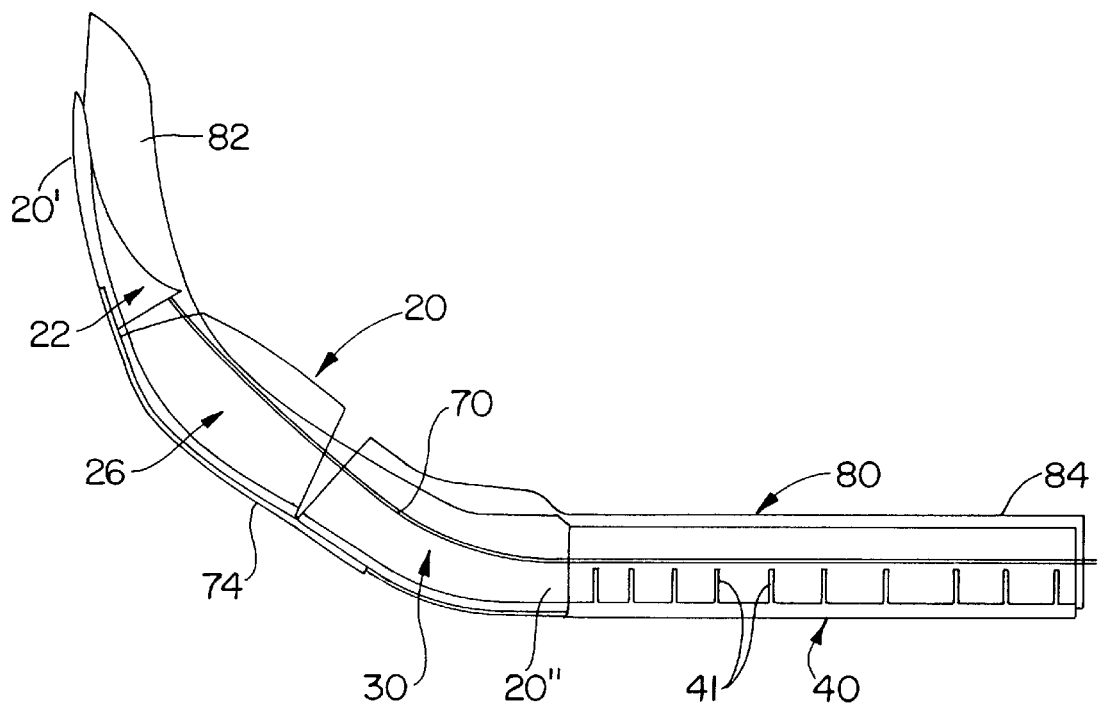
FIG. 5 is an isolated side view of the intubating assembly of the present invention with the guide assembly in its open orientation.
Figure 6:
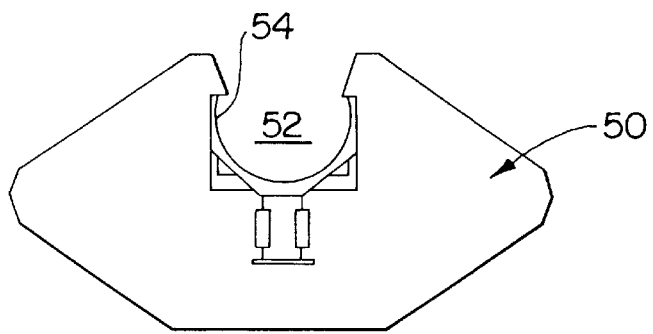
FIG. 6 is an isolated front view of the stopper of the present invention.
Figure 7:
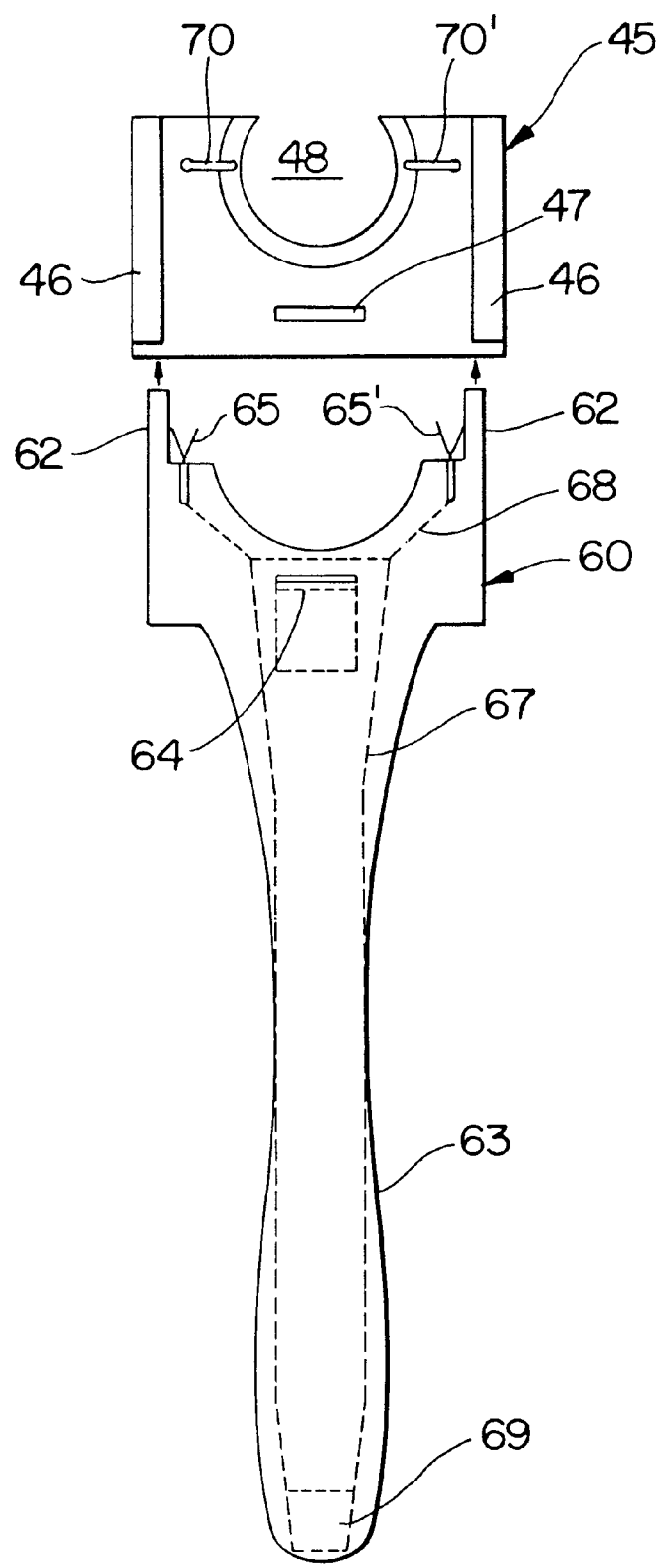
FIG. 7 is an exploded view of an alternative embodiment of the collar and handle assembly of the present invention.
Figure 8:
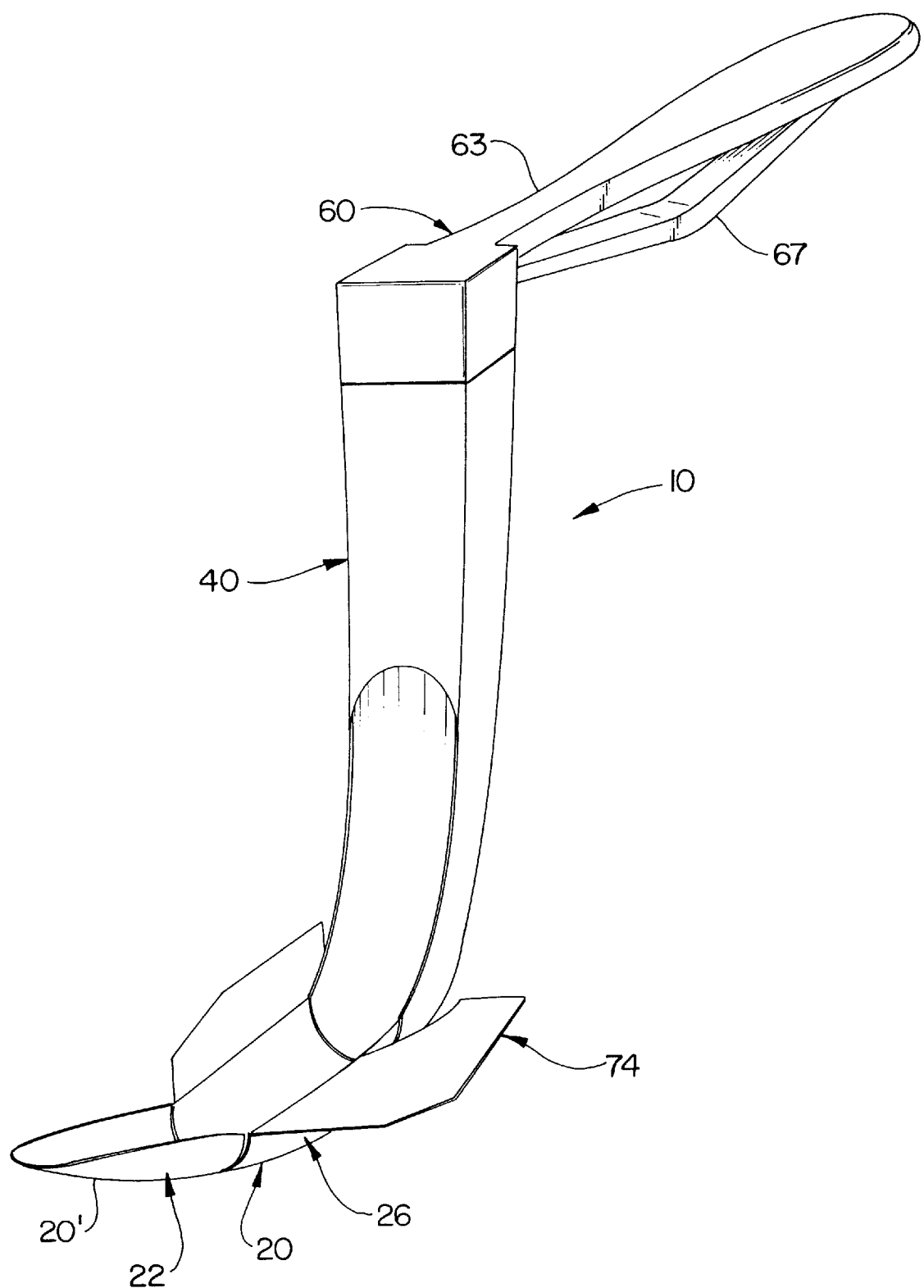
FIG. 8 is perspective view of a preferred embodiment of the present invention.

Looking specifically to the intubating assembly 10, it includes a guide assembly, generally 20. The guide assembly 20 is structured to at least partially receive the intubation tube 80 therein, and to at least partially and selectively conform the intubation tube 80 to its configuration, as will be described subsequently. Moreover, the guide assembly 20, which includes a distal end 20' and a proximal end 20", is comprised of at least a first introduction segment 22 and a second introduction segment 26. Preferably, however, the guide assembly 20 includes at least a first, a second and a third introduction segment 22, 26 and 30 so as to achieve a greater and more accurate curvature. In particular, the introduction segments 22, 26 and 30 are hingedly coupled to one another, and are thereby positionable between a closed orientation and an open orientation. Preferably, the closed orientation, as indicated in FIGS. 2 and 4, defines a generally curved configuration of the guide assembly 20, while the open configuration, as illustrated in FIGS. 1 and 5, defines a generally straight configuration of the guide assembly 20. As such, although only the two introduction segments 22 and 26 may be effectively utilized, the preferred inclusion of the third introduction segment 30, and/or additional introduction segments, provides a more effective and pronounced curvature in order to achieve more accurate guidance of the intubation tube 80 within the patient's airway, as will be described. Furthermore, it should be noted, that the generally straight configuration of the guide assembly 20 achieved by the open orientation of the introduction segments 22, 26 and 30, may still have a pronounced curvature, however for purposes of clarity the terms generally straight or straightened are utilized to denote a lessened curvature relative to that of the closed orientation. Additionally, the more pronounced curvature may indeed only be achieved at the distal end 20' of the guide assembly 20, so long as the curvature is sufficient to guide/direct the distal end of the intubation tube 80 towards the trachea, as will be described subsequently.

In the preferred embodiment, the guide assembly 20 includes an at least partially tubular configuration, extending at least partially along a length thereof. For example, the guide assembly 20 may include a generally C-shaped cross section along all or part of a length thereof. As such, facilitated positioning and preferably retention of the intubation tube 80 in the guide assembly 20 may be achieved, along with subsequent removal of the guide assembly 20 from the intubation tube 80, once the intubation tube 80 has been effectively positioned within the trachea 97 of the patient 90. Furthermore, it is seen that means to selectively retain the intubation tube 80 disposed within the guide assembly 20, when the guide assembly 20 is varied between its curved and straight configurations, are also provided. Specifically, these means, which may include a clip, strap, hook, cross bar or similar item, function to retain the intubation tube 80 securely within the guide segment 20 as the curvature of the guide assembly is varied. Accordingly, a modification in the curvature of the guide assembly 20 due to the positioning of the introduction segments 22, 26 and 30 between the closed and open orientations, will also result in a corresponding modification in the curvature of the intubation tube 80, and visa versa as permitted by the structure of the guide assembly 20. In the preferred embodiment, the guide assembly 20 is substantially enclosed at least one introduction segment, with the remaining introduction segment(s) having more of an open configuration to support and engage the distal end of the intubation tube 80. Still, however, it is preferred that an interior diameter of the introduction segments 26 and 30 be generally greater than that of the intubation tube 80 so as to not hinder subsequent removal of the guide assembly 20 from the intubation tube 80 once the intubation tube 80 has been effectively positioned within the trachea 97 of the patient 90. Moreover, if desired, such as when the guide assembly 20 is maintained within the patient's mouth during intubation or when the intubation tube 80 is merely being used to direct a concentrated flow of air at the trachea without actual intubation, a separate strap which extends from the guide assembly 20 around the patient's head may be incorporated. Also in such a use, the guide assembly 20 can act as a bite guard to prevent the biting of the intubation tube 80 by the patient.

Preferably coupled at generally a proximal end 20" of the guide assembly 20 is an introduction hub 40. The introduction hub 40 preferably includes a generally elongate, at least partially tubular configuration so as to receive the intubation tube 80 therein. Specifically, the introduction hub 40 is structured to be of a sufficient length so as to aid in the introduction and manipulation of the guide assembly 20 deep into the airway 93 of the patient 90. As will be described in further detail subsequently, during use of the intubating assembly 10 of the present invention, the guide assembly 20 will be substantially introduced into the airway 93 of the patient, and as a result the introduction hub 40 is preferably disposed to provide for handling and manipulation of the guide assembly 20 from outside of the mouth 92 of the patient 90.

Moreover, preferably disposed along an exterior surface of the introduction hub 40 are positioning indicia 41 or markers. The positioning indicia 41 are structured to indicate a length of introduction of the guide assembly 20, and therefore the intubation tube 80, into the patient during initial introduction. As such, a technician introducing the guide assembly 20 and the intubation tube 80 into the airway 93 of the patient is able to more effectively determine when the distal end 20' of the guide assembly 20, and therefore the distal end 82 of the intubation 80 is at certain specific points within the airway 93. For example, as will be described in greater detail subsequently, it is helpful to identify and recognize an approximate introduction length/depth at which the distal end 20' of the guide assembly 20 has extended to a point posterior of the tip of the epiglottis 95 of the patient.

So as to further facilitate the accurate introduction of the guide assembly 20 into the airway 93 of the patient 90, a stopper 50, may also be included. Specifically, the stopper 50 is structured to be adjustably coupled to the introduction hub 40 at a point corresponding the length of introduction of the guide assembly 20 into the airway 93 of the patient 90 which positions the distal end of 20' of the guide assembly 20, and therefore the distal end 82 of the intubation tube 80, at a point posterior of the tip of the epiglottis 95 of the patient 90. The stopper 50 itself, may take on any of a number of effective configurations, however, in the preferred embodiment, the stopper 50 includes a recessed portion 52 structured to removably receive the introduction hub 40 therein. Moreover, the previously described indicia 41 may define or correspond a series of channels or notches into which the stopper 50 can be introduced and or retained during use. In use, prior to introduction of the intubating assembly 10 into the mouth 92 of the patient 90, a preliminary measurement to facilitate determination of the effective length of introduction of the guide assembly 20 which will clear the tip of the epiglottis 95 of the patient is made.

Typically, such a measurement may be achieved by positioning the intubating assembly 10 on an exterior of the patient, and measuring from the corner of the patient's mouth 92 to the earlobe of the patient 90, as this distance provides a general indication of the length of the oral pharyngeal airway to be traversed in order to position the distal end 82 of the intubation tube 80 generally posterior of the tip of the epiglottis. Once this distance is measured, the stopper 50 is effectively positioned at the measured point, and introduction of the guide assembly 20 into the mouth 92 of the patient 90 can be achieved until the stopper 50 generally abuts the mouth/lips of the patient 90 to indicate that the effective introduction length has been reached.

In particular, the intubating assembly 10 of the present invention is structured to be introduced into the airway 93 of the patient 90 in the open orientation, thereby providing a direct, narrow, minimally obtrusive introduction superior to the tongue. Moreover, this initial introduction of the guide assembly 20 can be structured to generally follow a roof of the mouth of the patient, thereby ensuring that the guide assembly 20 is not accidentally introduced into the vallecula of the patient 90, and along a centered path to ensure that accidental introduction into the pyriform sinus is not caused. With regard to the centered path, it is noted that a preferred embodiment of the present invention may include one or more alignment elements 74 coupled to the guide assembly 20. The alignment elements 74 maintain the guide assembly generally centered within the airway of the patient during its introduction, thereby further facilitating accurate introduction of the intubation tube 80 into the trachea.

As indicated, the guide assembly 20 is preferably initially introduced into the patient 90 to a length sufficient to clear the tip of the epiglottis 95 of the patient 90, thereby ensuring that the intubation tube 80 is not directed into the patient's vallecula 94 that is bordered by the epiglottis 95. This initial introduction in the open orientation, however, should not extend too far so as to enter the esophagus 96 in the open orientation or the trachea in a closed or open orientation. Rather, once the desired initial introduction distance is achieved the guide assembly 20 is preferably manipulated into the closed orientation prior to further introduction of the intubation tube 80. Of course, it should be noted that in some instances introduction into the esophagus 96 is actually desired such that use of the present invention entirely in the open orientation can effectively accomplish this task.

To provide for the effective manipulation of the guide assembly 20 between the open and closed orientations, the intubating assembly 10 of the present invention further includes a positioning assembly. The positioning assembly is structured to selectively position at least the first and second, but preferably all of the introduction segments 22, 26 and 30, between the open orientation and closed orientation. As previously indicated, when in the open orientation, the intubation tube 80 is generally straightened to conform to the generally straight configuration of the guide assembly 20. As a result, direct introduction of the intubation tube 80 into the airway 93 of the patient 90 to the point posterior of the tip of the epiglottis 95 of the patient 90 may be easily achieved. Once introduction to that point is achieved, however, as indicated preferably by the engagement of the stopper 50, the positioning assembly is then structured to position the introduction segments 22, 26 and 30 into their closed orientation, thereby generally curving the intubation tube 80 and guide assembly 20. Preferably, it is noted that when the guide assembly 20 is in the closed orientation at least the distal end 82 of the intubation tube 80 is generally angled by the distal end 20' of the guide assembly 20 up towards the trachea 97 of the patient. Moreover, if desired, the first and second introduction segments may comprise a single unit with a distalmost region being hingedly/movably coupled to provide an upturn or abutment at the distal end 20' of the guide assembly 20 that tends to angle the distal end 82 of the intubation tube 80. Furthermore, structure may be provided so as to provide a series of set curvature points that can be achieved and maintained, either manually or mechanically, until affirmatively released.

As seen from the Figures, if straight introduction following the roof of the patient's mouth is continued too far, introduction of the intubation tube 80 into the esophagus 96 of the patient 90 will result. Conversely, following an opposite path of introduction with a completely curved device would result in introduction of the intubation tube into the vallecula 94. Utilizing the positioning assembly of the present invention, once introduction posterior of the epiglottis 95 is achieved, curvature and pointing of the distal end 82 of the intubation tube 80 is achieved so that further introduction of the intubation tube 80, such as by pushing the intubation tube 80 out of the guide assembly 20, will result in effective introduction of the intubation tube 80 into the trachea 97. Of course, subsequent to full introduction of the intubation tube 80 into the trachea 97 of the patient 90, the intubating assembly 10 is preferably, but not necessarily, removed from the intubation tube 80.

Looking to a preferred embodiment of the positioning assembly, the guide assembly 20 is preferably structured such that the normal, generally straightened curvature of the intubation tube 80 disposed therein will normally bias the introduction segments 22, 26 and 30 into their open orientation. As such, movement of the introduction segments 22, 26 and 30 is generally free so as to at least partially define the positioning assembly with the intubation tube 80. Of course, an additional biasing element may be provided to more affirmatively straighten the introduction segments 22, 26 and 30, as well as the intubation tube 80 disposed therein, should it include a normally curved, generally resilient configuration. Accordingly, when initially extending the guide assembly 20 into the patient 90, normal introduction allowing the positioning assembly to hold the generally straightened configuration is maintained.

Additionally, the positioning assembly includes a retraction assembly. In the preferred embodiment, the retraction assembly is structured to selectively urge at least the first and second introduction segment 22 and 26, but preferably all of the introduction segments 22, 26 and 30 into their closed orientation. In this embodiment, the retraction assembly includes at least one, but preferably a pair of elongate retraction segments 70 and 70' coupled to at least the first introduction segment 22. Moreover, the elongate retraction segments preferably include a pair of elongate wires 70 and 70' which are threaded through the introduction segments and are actuated so as to pull on at least the first introduction segment 22. Indeed, it is noted that connection of the elongate retraction segments 70 and 70' to the first introduction segment 22 is generally sufficient, as pulling on the first introduction segment 22 will generally cause all of the introduction segments of the guide assembly 20 to correspondingly contract into the closed orientation.

The preferred embodiment of the intubating assembly 10 of the present invention further includes a handle assembly 60. The handle assembly 60, which includes a preferably downwardly depending shaft 63 that is structured to be grasped by a user, and may be removably coupled to the guide assembly 20 if desired. Moreover, in the preferred embodiment, the handle assembly 60 is disposed at an end of the introduction hub 40. Specifically, the handle assembly 60 is preferably connected with a collar 45 coupled to the introduction hub 40. The collar 45, which may be integrally or fixedly secured in place includes a recessed area 48 into which the introduction hub 40 is removably positioned and retained. Furthermore, the collar 45 is structured to receive the elongate wires 70 and 70' accessibly disposed therein, and preferably looped therethrough, such that the pulling of the wires 70 and 70' at the collar 45 results in corresponding positioning of the guide assembly 20 into the closed orientation.

In an alternative embodiment wherein the handle assembly 60 is removably coupled to the collar 45, a pair of flanged track segments 46 are preferably provided at opposite ends of the collar 45. The track segments 46 are structured to correspondingly receive prongs 62 of the handle assembly 60 slidingly therein. Moreover, so as to generally lock the handle assembly 60 in place, a preferably biased lock element 64 is provided in the handle assembly 60, the lock element 64 being structured to extend into a corresponding slot 47 disposed in the collar 45. As a result, once the handle assembly 60 has locked in place, only by removing the lock element 64 from the slot 47 will corresponding slided removal of the handle assembly 60 from the collar 45 be achieved. Of course, it is noted that a variety of coupling assemblies may be incorporated, such as positioning the tracks on the handle assembly and the prongs on the collar 45, and indeed, the collar and handle assembly may be integrally coupled with one another and removably coupled to the introduction hub.

Figure 3:
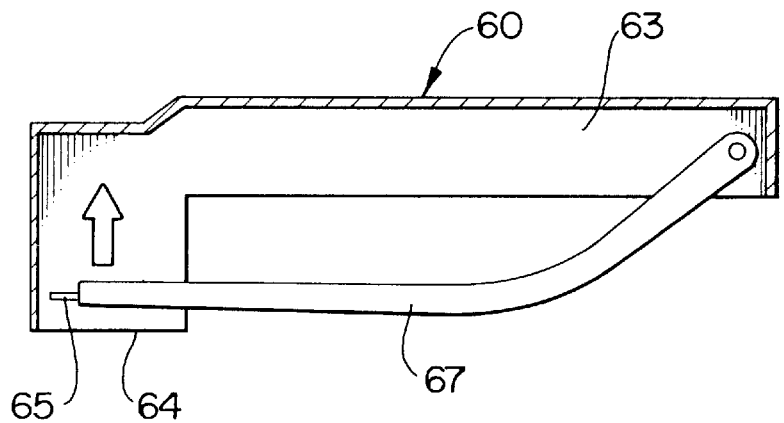
FIG. 3 is an isolated side view of the handle assembly of the present invention.

In addition to aiding with the manipulation of the guide assembly 20, the handle assembly 60 also preferably includes means to actuate the retraction assembly, namely the wires 70 and 70'. In this embodiment, the means to actuate the retraction assembly includes a preferably biased lever 67 that is hingedly coupled to the handle assembly 60. As illustrated in FIG. 3, an upper portion of the handle assembly 60 generally has some depth so as to permit a range of movement of the upper end of the lever 67. Conversely, a lower end of the lever 67 is hingedly coupled to the handle assembly 60, preferably at a lower end of the downwardly depend shaft 63 of the handle assembly 60. As such, a user is able to simultaneously grasp the downwardly depending shaft 63 and the lever 67 for corresponding actuation thereof. Disposed at an upper end of the lever 67 are a pair of engagement segments 65 and 65'. These engagement segments 65 and 65' are structured to matingly engage the loops of the elongate wires 70 and 70' which extend through the collar 45. Accordingly, as the upper end of the lever 67 is pulled away from the collar assembly 45, the wires 70 and 70' are pulled by the engagement segments 65 and 65' in order to urge the guide assembly 20 into the closed orientation. Moreover, this closed orientation of the guide assembly 20 is maintained until the lever is released and returned to its normal orientation. Of course, the lever 67 may be biased to its normal orientation utilizing a spring or like assembly, or as a result of the normal tendency of the guide assembly 20 to return to its open orientation, thereby releasing tension from the wires 70 and 70'. Furthermore, if desired in yet another embodiment, actuation of the handle assembly may also function to release the intubation tube 80 from the guide assembly 20. For example, the guide assembly 20 may include structure to secure the intubation tube 80 in place without permitting lateral sliding therethrough. When, however, the proper positioning of the guide assembly 20 is attained and a curvature thereof is desired, the intubation tube 80 can be released to permit its further introduction into the patient separate from the guide assembly 20.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents. For example, if desired, the positioning assembly may be modified such that the biasing element is structured to normally bias the introduction segments into their closed orientation, while the retraction assembly is structured to selectively urge the introduction segments into their open orientation.

Now that the invention has been described,

What is claimed is:

1. To position an intubation tube having a distal end, a proximal end and a generally resilient tubular configuration, into a trachea of a patient, an intubating assembly for supporting and guiding the intubation tube, said intubating assembly comprising:

a guide assembly, said guide assembly adapted to at least partially receive the intubation tube therein and adapted to selectively and at least partially conform the intubation tube to a curved configuration thereof, said guide assembly including at least a first introduction segment and a second introduction segment hingedly coupled by a hinged coupling to one another in an axial direction, wherein said hinged coupling permits relative rotation between said first introduction segment and said second introduction segment in an anterior direction transverse to said axial direction, said hinged coupling permitting rotation between a maximal relatively less curved configuration of said first introduction segment and said second introduction segment and a maximal relatively more curved configuration of said first introduction segment and said second introduction segment, said maximal relatively less curved configuration of said first introduction segment and said second introduction segment being curved from a straight alignment of said first introduction segment and said second introduction segment in the anterior direction, said hinged coupling preventing relative rotation between said first introduction segment and said second introduction segment beyond said maximal relatively less curved configuration of said first introduction segment and said second introduction segment in a posterior direction opposite said anterior direction, said hinged coupling preventing relative rotation between said first introduction segment and said second introduction segment in a lateral direction transverse to said axial direction and transverse to said anterior direction, and a positioning assembly structured to selectively position at least said first and said second introduction segments between said maximal relatively less curved configuration of said first introduction segment and said second introduction segment and said maximal relatively more curved configuration of said first introduction segment and said second introduction segment, whereby said guide assembly can facilitate direct introduction of an intubation tube into an airway of the patient to a point posterior of a tip of an epiglottis of the patient in the maximal relatively less curved configuration, and in the maximal relatively more curved configuration, generally curve an intubation tube when disposed in said guide assembly and thereby angle the distal end of the intubation tube towards the trachea of the patient such that subsequent introduction of the intubation tube into the airway of the patient is directed into the trachea of the patient.

2. An intubating assembly as recited in claim 1 wherein said guide assembly includes at least a third introduction segment hingedly coupled by a further hinged coupling to said second introduction segment, in an axial direction, wherein said further hinged coupling permits relative rotation between said second introduction segment and third second introduction segment in an anterior direction transverse to said axial direction, said further hinged coupling permitting rotation between a maximal relatively less curved configuration of said second introduction segment and said third introduction segment and a maximal relatively more curved configuration of said second introduction segment and said third introduction segment, said maximal relatively less curved configuration of said second introduction segment and said third introduction segment being curved from a straight alignment of said second introduction segment and said third introduction segment in the anterior direction, said further hinged coupling preventing relative rotation between said second introduction segment and said third introduction segment beyond said maximal relatively less curved configuration of said second introduction segment and said third introduction segment in a posterior direction opposite said anterior direction, said further hinged coupling preventing relative rotation between said second introduction segment and said third introduction segment in a lateral direction transverse to said axial direction and transverse to said anterior direction.

3. An intubating assembly as recited in claim 1 wherein said positioning assembly comprises:
  a retraction assembly structured to selectively urge at least said first and said second introduction segments into said maximal relatively more curved configuration.

4. An intubating assembly as recited in claim 3 wherein said retraction assembly includes an elongate retraction segment coupled to at least said first introduction segment and structured to be actuated so as to pull said first introduction segment, and therefore said guide assembly, into said maximal relatively more curved configuration.

5. An intubating assembly as recited in claim 4 wherein said retraction segment includes an elongate wire.

6. An intubating assembly as recited in claim 4 further including a handle assembly structured to be coupled to said guide assembly so as to facilitate manipulation and introduction thereof into the airway of the patient, said handle assembly including means to actuate said retraction assembly.

7. An intubating assembly as recited in claim 6 wherein said retraction segment includes a pair of elongate wires extending through said guide assembly.

8. An intubating assembly as recited in claim 7 wherein said means to actuate said retraction assembly includes a biased lever hingedly coupled to said handle assembly at a lower end thereof and coupled to said pair of elongate wires at an upper end thereof so as to pull on said pair of elongate wires upon inward movement of said upper end thereof.

9. An intubating assembly as recited in claim 1 further including an introduction hub coupled in a rigid, non-pivotal manner to a proximal end of said guide assembly and being generally elongate so as to facilitate introduction of said guide assembly into the airway of the patient.

10. An intubating assembly as recited in claim 9 wherein said introduction hub includes positioning indicia disposed thereon and structured to indicate a length of introduction of said guide assembly, whereby when an intubation tube is positioned in the assembly, its length of introduction into the airway of the patient so as to reach said point posterior of the tip of the epiglottis of the patient can be determined without visualization of the throat.

11. An intubating assembly as recited in claim 10 further including a stopper structured to be adjustably coupled to said introduction hub at a point corresponding said length of introduction of said guide assembly.

12. An intubating assembly as recited in claim 9 further including a stopper structured to be adjustably coupled to said introduction hub at a point corresponding a length of introduction of said guide assembly into the airway of the patient whereby an intubation tube positioned in the assembly can be determined to reach said point posterior of the tip of the epiglottis of the patient without visualization of the throat.

13. An intubating assembly as recited in claim 9 further including a handle assembly structured to be coupled to said introduction hub so as to facilitate manipulation and introduction of said guide assembly into the airway of the patient.

14. An intubating assembly as recited in claim 1 further including a handle assembly structured to be coupled to said guide assembly so as to facilitate manipulation and introduction thereof into the airway of the patient.

15. An intubating assembly as recited in claim 1 wherein said guide assembly incudes a generally tubular configuration.

16. An intubating assembly as recited in claim 1 wherein said guide assembly includes a generally c-shaped cross section configuration structured to facilitate positioning of an intubation tube therein and subsequent removal of said guide assembly from the patient airway subsequent to introduction of the intubation tube into the trachea of the patient.

17. An intubating assembly as recited in claim 1 further including means to selectively retain an intubation tube when disposed in said guide assembly and so as to at least partially conform an intubation tube to curvature of said guide assembly.

18. An intubating assembly as recited in claim 1 further including an alignment element coupled to said guide assembly on each lateral side of said guide assembly and structured to maintain said guide assembly centered during introduction into an airway of the patient and thereby avoid accidental introduction into a pyriform sinus of the patient.

19. The intubating assembly of claim 10, wherein the hinged coupling prevents relative axial translation between the first introduction segment and the second introduction segment in either of the maximal relatively less curved configuration of said first introduction segment and said second introduction segment and the maximal relatively more curved configuration of said first introduction segment and said second introduction segment, whereby indication of predetermined external measurement of length of guide assembly to be inserted into the patient passageway is maintained during insertion of guide assembly.

20. To position an intubation tube having a distal end, a proximal end and a generally resilient tubular configuration, into a trachea of a patient, an intubating assembly comprising:
  an intubation tube;
  a guide assembly, said guide assembly at least partially receiving the intubation tube therein and selectively and at least partially conforming the intubation tube to a configuration thereof,
  said guide assembly including at least a first introduction segment and a second introduction segment hingedly coupled by a hinged coupling to one another in an axial direction, wherein said hinged coupling permits relative rotation between said first introduction segment and said second introduction segment in an anterior direction transverse to said axial direction, said hinged coupling permitting rotation between a maximal relatively less curved configuration of said first introduction segment and said second introduction segment and a maximal relatively more curved configuration of said first introduction segment and said second introduction segment, said maximal relatively less curved configuration of said first introduction segment and said second introduction segment being curved from a straight alignment of said first introduction segment and said second introduction segment in the anterior direction, said hinged coupling preventing relative rotation between said first introduction segment and said second introduction segment beyond said maximal relatively less curved configuration of said first introduction segment and said second introduction segment in a posterior direction opposite said anterior direction, said hinged coupling preventing relative rotation between said first introduction segment and said second introduction segment in a lateral direction transverse to said axial direction and transverse to said anterior direction; and a positioning assembly structured to selectively position at least said first and said second introduction segments between said maximal relatively less curved configuration of said first introduction segment and said second introduction segment and said maximal relatively more curved configuration of said first introduction segment and said second introduction segment, whereby said guide assembly can facilitate direct introduction of intubation tube into an airway of the patient to a point posterior of a tip of an epiglottis of the patient in the maximal relatively less curved configuration, and in the maximal relatively more curved configuration, generally curve the intubation tube and thereby angle the distal end of the intubation tube towards the trachea of the patient such that the intubation tube is directed into the trachea of the patient.

* * * * *